United States Patent
Shen et al.

(10) Patent No.: US 10,586,670 B2
(45) Date of Patent: Mar. 10, 2020

(54) WIRELESS DIAGNOSIS SYSTEM POWER SUPPLY

(71) Applicant: ZUMAX MEDICAL CO., LTD., Suzhou, Jiangsu (CN)

(72) Inventors: Shunguo Shen, Jiangsu (CN); Xiaohua Yang, Jiangsu (CN); Xiaotian Chen, Jiangsu (CN)

(73) Assignee: ZUMAX MEDICAL CO., LTD., Suzhou, Jiangsu (CN)

( * ) Notice: Subject to any disclaimer, the term of this patent is extended or adjusted under 35 U.S.C. 154(b) by 163 days.

(21) Appl. No.: 15/560,133

(22) PCT Filed: Sep. 2, 2015

(86) PCT No.: PCT/CN2015/088839
§ 371 (c)(1),
(2) Date: Sep. 20, 2017

(87) PCT Pub. No.: WO2016/155235
PCT Pub. Date: Oct. 6, 2016

(65) Prior Publication Data
US 2018/0102230 A1    Apr. 12, 2018

(30) Foreign Application Priority Data
Mar. 27, 2015    (CN) .................. 2015 1 01410258

(51) Int. Cl.
*H01H 9/00*    (2006.01)
*H01H 50/18*    (2006.01)
(Continued)

(52) U.S. Cl.
CPC ......... *H01H 50/18* (2013.01); *A61B 1/00029* (2013.01); *A61B 5/00* (2013.01);
(Continued)

(58) Field of Classification Search
CPC .......... H01H 50/06; H01H 50/18; A61N 5/06; A61N 1/20
(Continued)

(56) References Cited

U.S. PATENT DOCUMENTS 5,413,590 A * 5/1995 Williamson ............ A61N 1/20
607/75
5,971,804 A * 10/1999 Gallagher ............... G06F 1/189
333/238

(Continued)

FOREIGN PATENT DOCUMENTS

CN    2925514 Y    7/2007
CN    204181643 U    3/2015

OTHER PUBLICATIONS

International Search Report for Application No. PCT/CN2015/088839, dated Nov. 11, 2015.

Primary Examiner — Shawki S Ismail
Assistant Examiner — Lisa N Homza
(74) Attorney, Agent, or Firm — Knobbe, Martens, Olson & Bear, LLP

(57) ABSTRACT

Disclosed is a wireless diagnosis system power supply, which is not connected with an external power supply, and comprises a shell (1), a battery pack (2) provided within the shell, an electrical module (3) connected with the battery pack to adjust the voltage and the current, and a cable handle (4) connected with the electrical module. The power supply provides independent power supply directly without connecting with an external power network, and achieves a reasonable arrangement, a compact structure, a small size, a long service life, power saving, safety and reliability, convenience in clinical use, and high utilization rate of clinic space; and the whole system is portable and easy to install.

6 Claims, 1 Drawing Sheet

(51) Int. Cl.
*A61B 1/00* (2006.01)
*A61B 5/00* (2006.01)
*A61N 1/20* (2006.01)
*A61N 5/06* (2006.01)
*A61B 1/227* (2006.01)
*A61B 3/12* (2006.01)

(52) U.S. Cl.
CPC .................. *A61N 1/20* (2013.01); *A61N 5/06* (2013.01); *A61B 1/00108* (2013.01); *A61B 1/227* (2013.01); *A61B 3/12* (2013.01); *A61B 5/0013* (2013.01); *A61B 2560/0204* (2013.01)

(58) Field of Classification Search
USPC ........................................................ 335/203
See application file for complete search history.

(56) References Cited

U.S. PATENT DOCUMENTS

| | | | | |
|---|---|---|---|---|
| 6,185,462 | B1* | 2/2001 | Cho | A61N 1/20 607/75 |
| 9,229,504 | B1* | 1/2016 | Marr | G06F 1/189 |
| 9,320,166 | B1* | 4/2016 | Marr | H05K 7/14 |
| 2001/0011314 | A1* | 8/2001 | Gallagher | G06F 9/4406 710/302 |
| 2008/0131855 | A1* | 6/2008 | Eggert | G09B 23/30 434/266 |
| 2008/0138778 | A1* | 6/2008 | Eggert | G09B 23/28 434/262 |
| 2008/0138779 | A1* | 6/2008 | Eggert | G09B 23/281 434/266 |
| 2008/0138780 | A1* | 6/2008 | Eggert | G09B 23/28 434/266 |
| 2009/0008374 | A1* | 1/2009 | Fosbinder | B23K 9/1006 219/130.21 |
| 2009/0148822 | A1* | 6/2009 | Eggert | G09B 23/281 434/271 |
| 2013/0027157 | A1* | 1/2013 | Niimi | F02N 11/087 335/2 |
| 2014/0153159 | A1* | 6/2014 | Hazel | H02J 1/08 361/602 |
| 2015/0311656 | A1* | 10/2015 | Lai | H01R 31/065 439/620.22 |
| 2016/0134381 | A1* | 5/2016 | Malinin | H04B 1/707 375/130 |
| 2016/0243711 | A1* | 8/2016 | Carrasco | B26B 7/00 |
| 2016/0372009 | A1* | 12/2016 | Eggert | G09B 23/28 |
| 2017/0324262 | A1* | 11/2017 | Kosugi | H01M 4/5825 |
| 2019/0054318 | A1* | 2/2019 | Goer | A61N 5/1067 |

* cited by examiner

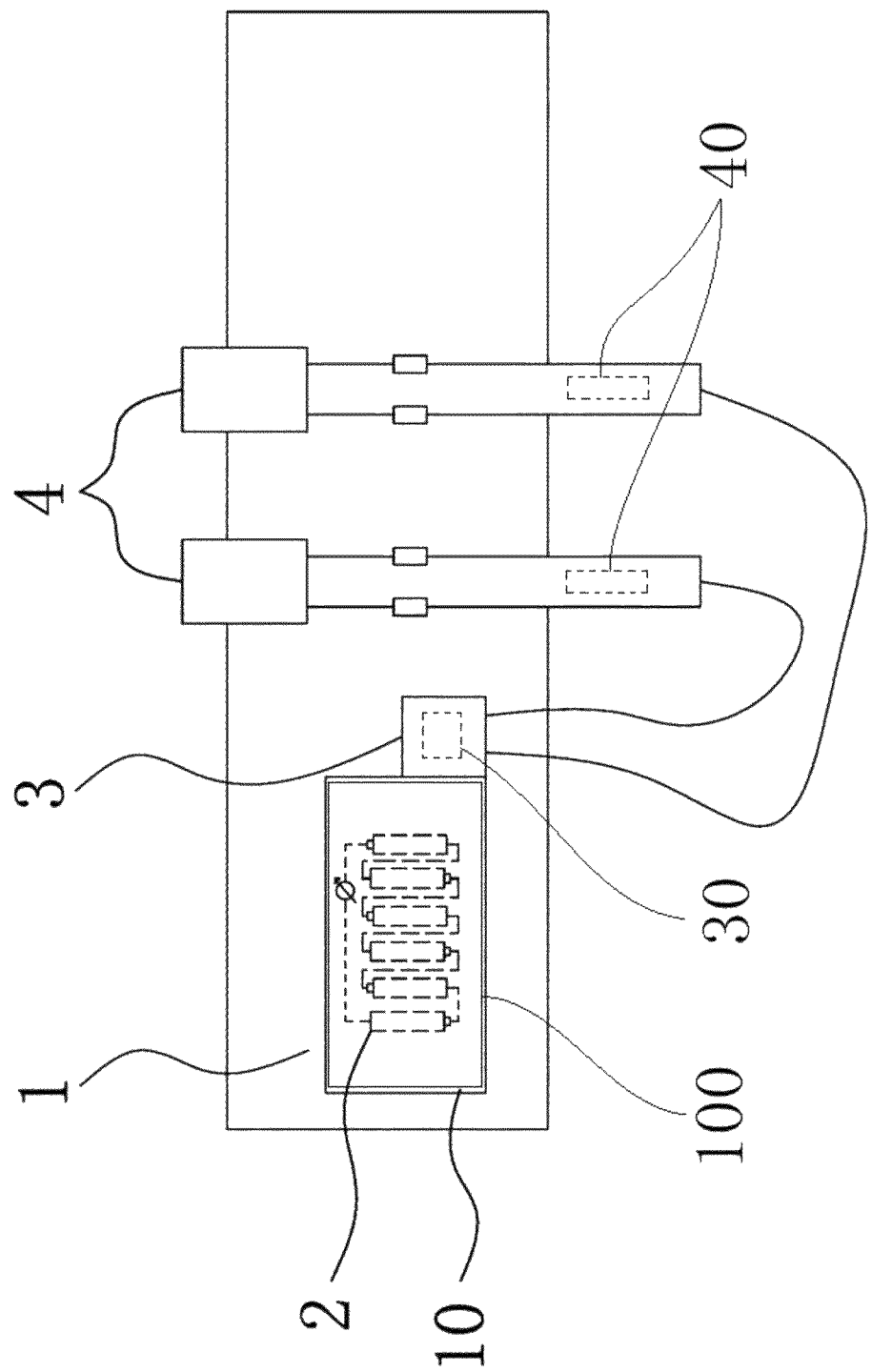

WIRELESS DIAGNOSIS SYSTEM POWER SUPPLY

TECHNICAL FIELD OF THE INVENTION

The present application relates to the field of clinical diagnosis instruments, in particular to a wireless diagnosis system power supply.

BACKGROUND OF THE INVENTION

The diagnosis system power supply mainly is to supply power for hand-held diagnosis equipment, for example in ophthalmoscope, otoscope and other ENT inspection equipment, and the power supply is widely used in the hospital. A conventional diagnosis system power supply is usually powered by a transformer, and has a large volume and poor safety, and the transformer is easy to aging after using for a period of time, which results in that the diagnosis system power cannot be used. Secondly, the power supply is usually installed on the wall, and cannot move, which makes it not convenient for clinical use, such as in the mobile cart or in the ambulance.

An existing technology replacing an internal transformer supplies power to the diagnosis system by selecting an adapter, although this method improves the diagnosis system power supply in safety and volume, the diagnosis system power supply is still unable to install within a mobile cart or an ambulance.

SUMMARY OF THE INVENTION

The present application is aimed at providing a wireless diagnosis system power supply which is able to power hand-held diagnosis equipment independently.

To achieve the above purpose, the technical schemes employed by the present application are:

a wireless diagnosis system power supply, which is not connected with an external power supply, comprises a shell, a battery pack provided within the shell, an electrical module connected with the battery pack to adjust the voltage and the current, and a cable handle connected with the electrical module.

Preferably, the battery pack comprises one or more batteries connected in series.

Preferably, the batteries are disposable batteries or rechargeable batteries.

Preferably, the electrical module is provided with an inductive switch; when the cable handle is removed from the shell, the inductive switch is open, and the electrical module is switched on; and when the cable handle is laid on the shell, the inductive switch is closed, and the electrical module is switched off.

Preferably, the electrical module is provided within the shell or within the cable handle.

Preferably, a timing piece capable of cutting off the power automatically is provided within the cable handle.

Preferably, the shell has a chamber capable of placing the battery pack, and the chamber has a detachable lid.

Due to the utilization of the above technical schemes, the present application has the following advantages over the prior art:

The present application provides independent power supply directly without connecting with an external power network, and achieves a reasonable arrangement, a compact structure, a small volume, a long service life, power saving, safety and reliability, convenience in clinical use, and high utilization rate of clinic space, and the whole system is portable and easy to install.

BRIEF DESCRIPTION OF THE DRAWINGS

FIG. 1 is a schematic structure diagram of the present application;

wherein: 1—shell; 10—chamber; 100—detachable lid; 2—battery pack; 3—electrical module; 30—inductive switch; 4—cable handle; 40—timing piece.

DETAILED DESCRIPTION OF EXEMPLARY EMBODIMENTS

In the following, the present application is further described to combining with the accompanying drawing:

A wireless diagnosis system power supply as shown in FIG. 1, is not connected with an external power supply, and comprises a shell 1, a battery pack 2 provided within the shell 1, an electrical module 3 connected with the battery pack 2 to adjust the voltage and the current, and a cable handle 4 connected with the electrical module 3, the cable handle 4 being laid on the shell 1. Wherein, the shell 1 serves as a support of the whole power supply, and may be movably hanged on the wall or be carried around.

The battery pack 2 comprises one or more batteries, and when multiple batteries are used, the batteries are connected in series, and the batteries are disposable batteries or rechargeable batteries. The shell 1 has a chamber 10 capable of placing the battery pack 2, and the chamber 10 has a detachable lid 100 to facilitate the storage and replacement of the battery pack 2.

The electrical module 3 is used to adjust the voltage and the current of the power supplying of the battery pack 2. For example, the battery pack 2 is formed by three 1.5V batteries connected in series and has a voltage of 4.5V, which is adjusted to 3.5V by means of the electrical module 4. The electrical module 3 is provided with an inductive switch 30; when the cable handle 4 is taken down, the inductive switch 30 is open, and the electrical module 3 is switched on; and when the cable handle 4 is laid on the shell 1, the inductive switch 30 is closed, and the electrical module 3 is switched off; the inductive switch 30 may be selected to be a Hall switch and the like, and can switch over without manual operation when use. The electrical module 3 may be provided within the shell 1 or within the cable handle 4 according to requirements.

The cable handle 4 may be connected with a diagnosis illumination device which is connected with the electrical module 3 via a wire, and a timing piece 40 capable of cutting off the power automatically is provided within the cable handle 4, for example, when the cable handle 4 is not used after being taken down for a long time, the timing piece 40 may cut off the power automatically. The cable handle 4 may be provided to be one or more, and may be provided with multiple diagnosis illumination devices at the same time.

The entire power supply uses the optimized integration process, the shell 1 uses a fully enclosed dustproof design, and all components are internally installed, the power supply has a small volume and a long service life.

The embodiments described above are only for illustrating the technical concepts and features of the present application, and intended to make those skilled in the art being able to understand the present application and thereby implement it, and should not be concluded to limit the protective scope of this application. Any equivalent variations or modifications according to the spirit of the present application should be covered by the protective scope of the present application.

The invention claimed is:

1. A wireless diagnosis system power supply, the power supply is not connected with an external power supply, comprising: a shell, a battery pack provided within the shell, an electrical module connected with the battery pack to adjust the voltage and the current, and a cable handle connected with the electrical module, wherein the electrical module is provided with an inductive switch; when the cable handle is removed from the shell, the inductive switch is open, and the electrical module is switched on; and when the cable handle is laid on the shell, the inductive switch is closed, and the electrical module is switched off.

2. The wireless diagnosis system power supply according to claim 1, wherein the battery pack comprises one or more batteries connected in series.

3. The wireless diagnosis system power supply according to claim 2, wherein the batteries are disposable batteries or rechargeable batteries.

4. The wireless diagnosis system power supply according to claim 1, wherein the electrical module is provided within the shell or within the cable handle.

5. The wireless diagnosis system power supply according to claim 1, wherein a timing piece is provided within the cable handle.

6. The wireless diagnosis system power supply according to claim 1, wherein the shell has a chamber capable of placing the battery pack, and the chamber has a detachable lid.

* * * * *